United States Patent [19]

Gilles et al.

[11] Patent Number: 4,528,158

[45] Date of Patent: Jul. 9, 1985

[54] AUTOMATIC SAMPLING SYSTEM

[75] Inventors: Pieter Gilles, Rijswyk, Netherlands; Jean-Claude Schmitt, Draveil, France

[73] Assignee: Baird Corporation, Bedford, Mass.

[21] Appl. No.: 388,485

[22] Filed: Jun. 14, 1982

[51] Int. Cl.³ .................... G01N 1/14; G01N 35/00
[52] U.S. Cl. .................... 422/63; 73/864.22;
422/65; 422/68; 422/100; 436/43; 436/47;
436/49; 436/54; 436/73; 436/179; 436/180
[58] Field of Search ........... 73/864.21, 864.22, 864.12;
134/104, 111, 109; 137/544; 141/59; 173/10;
219/74; 422/63–65, 67, 68, 100; 436/43, 47, 49,
54, 73, 179, 180; 239/304, 310, 398; 222/630;
285/133 R, 132, 343

[56] References Cited

U.S. PATENT DOCUMENTS

| | | | |
|---|---|---|---|
| 3,295,870 | 1/1967 | Seablom | 285/343 X |
| 3,649,218 | 3/1972 | Pontigny | 73/864.12 X |
| 3,795,149 | 3/1974 | Gillette et al. | 73/864.22 X |
| 3,842,680 | 10/1974 | Vollick et al. | 422/100 X |
| 3,971,394 | 7/1976 | Osborne | 134/104 |
| 4,108,608 | 8/1978 | Maher, Jr. et al. | 73/864.12 |
| 4,234,779 | 11/1980 | Willems | 219/74 X |
| 4,271,123 | 6/1981 | Curry et al. | 436/164 X |
| 4,298,018 | 11/1981 | Haggard | 222/630 X |
| 4,318,885 | 3/1982 | Suzuki et al. | 422/63 X |

Primary Examiner—Michael Marcus
Assistant Examiner—Michael S. Gzybowski
Attorney, Agent, or Firm—Morse, Altman & Dacey

[57] ABSTRACT

An automatic sampling system and method for introducing a diluted viscous sample into an instrument for analysis for trace elements. The automatic sampling system includes a tube assembly, a member for mounting the tube assembly in proper relation, means for maintaining, between sampling, the free end of the tube assembly in a cleaning solution, and means for inserting the free end of the tube assembly into a sample contained within a container. Preferably, the instrument is a spectrometer, the samples are organic and aqueous samples, such as oils, brines, sludges, plating solutions and the like, and the trace elements include wear metals and also other elements, such as calcium, barium, zinc, sodium, magnesium, boron, phosphor and the like.

6 Claims, 5 Drawing Figures

AUTOMATIC SAMPLING SYSTEM

BACKGROUND OF THE INVENTION

1. Field of the Invention

The present invention relates generally to sampling systems and, more particularly, to an automatic sampling system and method for introducing a diluted viscous sample into an instrument, such as a spectrometer, for analysis for trace elements.

2. The Prior Art

Automatic sampling systems are in widespread use today in industrial, clinical and medical laboratories. Typically, such systems include a mechanism, such as a tray, designed to hold a plurality of sample containers and present these, one by one, to a sampling station and, a further mechanism, such as a mechanical arm, designed to introduce the free end of a nozzle or tube into the sample contained within the container that has been presented at the sampling station. For most applications, samples must be diluted and mixed with an appropriate solvent. Preferably, this is done prior to the sample's introduction into the sample container. Thus, the sample solution already is properly diluted and mixed with the appropriate solvent when it arrives at the sampling station. In other instances, the instrument performing the analysis on the sample itself is provided with a suitable device to dilute and mix the sample when the same is first introduced into the instrument or shortly thereafter. Some of these devices are incorporated in the instrument or are attachments adjacent the entrance ports thereof. Further, most of these devices operate on samples or sample solutions that are for the most part non-viscous or rather low in viscosity. The demands for a sampling system operating on viscous samples, such as oils, brines, sludges and the like, are higher both in terms of aspiration, dilution and mixing than is the case for systems operating on non-viscous or lowly viscous samples. Not only is a viscous substance more difficult to aspirate, but it also is harder to dilute, harder to mix, and still harder to cleanse between sampling. These difficulties add up: to reduce sample throughput, to increase operator manipulations, thus to increase cost per sample.

SUMMARY OF THE INVENTION

It is a principal object of the present invention to overcome the above disadvantages by providing an automatic sampling system of improved design and method for introducing a diluted viscous sample into an instrument for trace element analysis.

More specifically, it is an object of the present invention to provide an automatic sampling system that essentially comprises a tube assembly, a two part member for mounting the tube assembly and maintaining its free end, in between sampling, in a cleaning solution, means for automatically inserting the free end of the tube assembly into a sample held within a container, and means for moving the tube assembly between an operative and an inoperative position and also for moving it, when in the inoperative position, between a sampling station and a cleaning station. The tube assembly includes an inner tube and an outer tube concentric about the inner tube, with the free end of the inner tube being offset from the free end of the outer tube. A further tube also is mounted in the member but at an angle to and communicating with the outer tube. The automatic sampling system is simple in design and construction, and can be retrofitted onto existing instruments equipped either with no automatic sampling systems or with other less desirable systems. Preferably, the instrument is a spectrometer, such as an inductively coupled plasma atomic fluorescence spectrometer. Preferably, the samples are organic and aqueous samples, such as oils, brines, sludges, plating solutions and the like, and the trace elements include wear metals and also other elements, such as calcium, barium, zinc, sodium, magnesium, boron, phosphor and the like.

Other objects of the present invention will in part be obvious and will in part appear hereinafter.

The invention accordingly comprises the automatic sampling system of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings wherein.

DETAILED DESCRIPTION OF THE PREFERRED EMBODIMENT

Figures 1, 2, 3:
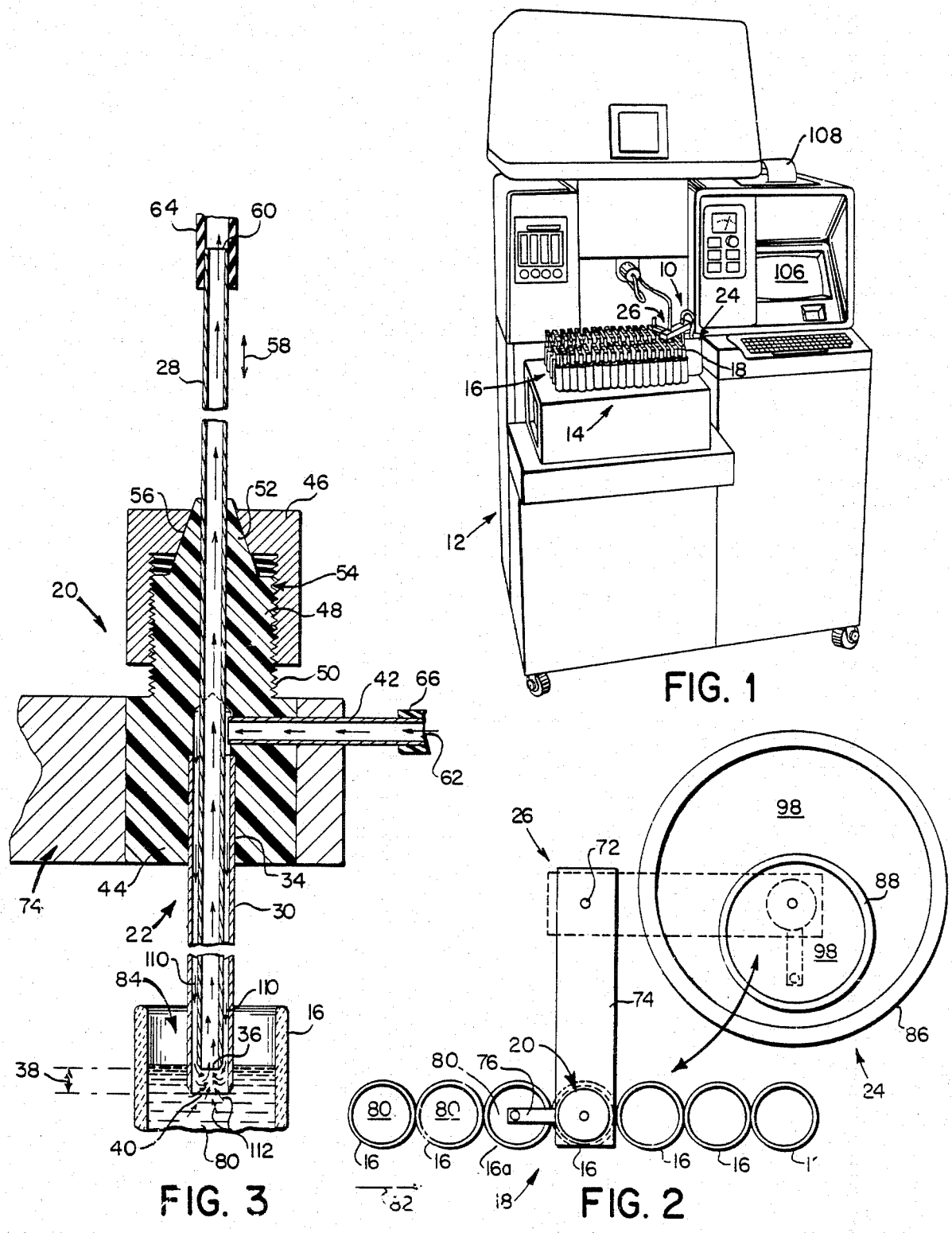
FIG. 1 is a perspective view of an instrument designed for analyzing samples for trace elements and featuring an automatic sampling system constructed in accordance with the present invention.
FIG. 2 is a plan schematic, illustrating portions of the automatic sampling system shown in FIG. 1.
FIG. 3 is a vertical elevation, partly in section, illustrating further portions of the automatic sampling system shown in FIG. 1.

Generally, an automatic sampling system 10 constructed in accordance with the invention is illustrated in FIG. 1 as attached to an instrument 12, such as a spectrometer, designed for analysis of unknown samples in solution. Preferably, the instrument 12 is an inductively coupled atomic fluorescence spectrometer, such as that disclosed in U.S. Pat. No. 4,300,834 and assigned to a common assignee. The automatic sampling system 10 is intended to introduce, automatically and seriatim, a plurality of viscous samples and dilute these samples in a proper ratio during the very process of their introduction into the instrument 12. Preferably, the automatic sampling system 10 is designed to increase sample throughput through the instrument 12. This is achieved principally by automating some functions, including on-stream dilution of the samples and cleansing the system 10 in between sampling. Thus, the frequency of operator intervention is reduced. Preferably, the viscous samples are organic and aqueous samples, such as oils, brines, sludges, plating solutions and the like. Preferably, these viscous samples are intended for analysis for trace elements, such as wear metals and other elements including calcium, barium, zinc, sodium, magnesium, boron, phosphor and the like. It will be appreciated that the handling and the transporting via tubes of viscous samples presents considerably more difficulties than is the case involving non-viscous or lowly-viscous samples. These difficulties are further magnified when these viscous samples have to be diluted in a proper ratio, and thereafter and before the next sampling, the entire sampling system 10 must be thoroughly cleaned, both inside and outside at the tip, lest measurements are affected by unwanted leftovers (crossovers) from the previous sample.

The automatic sampling system 10 for introducing a diluted viscous sample into the instrument 12 essentially comprises a tray 14 designed to hold a plurality of sample containers 16 and to present them seriatim to a sampling station 18, a member 20 operatively mounted thereat, a tube assembly 22 secured in the member 20, cleaning means 24 mounted adjacent the sampling station 18, and means 26 for moving the tube assembly 22 between an operative position engaging either one of the sample containers 16 or the cleaning means 24 and an inoperative position being free of both and also for moving the tube assembly 22, when in the inoperative position, laterally between the sampling station 18 and the cleaning means 24. Normally, the free end of the tube assembly 22 is disposed, except when sampling, in the cleaning means 24.

As may be best observed in FIG. 3, the tube assembly 22 includes an inner tube 28 and an outer tube 30 mounted concentric about the inner tube 28. Both tubes 28 and and 30 are secured within appropriate bores 32 and 34 extending centrally and lenthwise through the member 20. It will be noted that the inner tube 28 extends in two directions from the member 20, whereas the outer tube 30 extends therefrom in but one direction. It will be further noted that the free end 36 of the inner tube 28 is offset by short distance 38 from the free end 40 of the outer tube 30. The significance of this offset will become evident below. A further tube 42 also is secured in the member 20 but at an angle to and communicating with the outer tube 30.

Preferably, this angle is 90°. Each of the tubes 30 and 42 is a rigid metal tube, such as stainless steel. Tube 28 also is rigid and formed of teflon or stainless steel. The member 20 is formed of two parts: a plastic part 44, preferably made from polypropylene, or the like, and a metal part 46, preferably made from stainless steel. The plastic part 44 further is formed with a male section 48 having an externally-threaded portion 50 and a dome-like portion 52. The metal part 46 is designed to fit over the male section 48 of the plastic part 44, and is formed with an internally-threaded portion 54 to mesh with the externally-threaded portion 50 of the male section 48 and a central bevelled portion 56 designed to fit over the dome-like portion 52. It will be appreciated that by tightening the metal part 46 about the plastic part 44, particularly the dome-like portion 52 thereof, the latter will be pressed tightly about the inner tube 28, preventing thus the tube's 28 translatory motion, as indicated by the double-headed arrow 58, within the member 20. In contrast, by loosening the metal part 46 about the plastic part 44, the tube 28 can be moved in translation within the member 20, allowing thereby an adjustment in the distance 38 of the offset between the free end 36 of the inner tube 28 and the free end 40 of the outer tube 30. The tubes 30 and 42 are, by contrast, firmly anchored within the member 20. The other ends 60 and 62 of the tubes 28 and 42 respectively, are intended to be connected to flexible tubings 64 and 66, respectively, please observe FIG. 4.

A pair of pumps 68 and 70, which preferably are peristaltic pumps, are respectively connected to the tubings 64 and 66. Preferably, the pumps 68 and 70 are connected operatively and are operated simultaneously and also constantly while the instrument 12 is in use. Yet, the pumps 68 and 70 pump at different rates, with the pump 68 pumping at a higher rate than does the pump 70. This different rate of pumping is effected, as known, simply by using pump tubes of different internal diameters as between the pumps 68 and 70. The pump tube with the larger internal diameter is wound about the pump 68, while the pump tube with the smaller internal diameter is wound about the pump 70. By simply changing the pump tubes to a larger or smaller size, the respective rates of pumping can be conveniently adjusted, as desired.

The cleaning means 24 and the moving means 26 for the tube assembly 22 are best described with reference to FIGS. 2 and 5. The function of the moving means 26 essentially is twofold: first, to move the tube assembly 22 in translation between an operative (down or engaging) position and an inoperative (up or disengaging) position and, second, to move the tube assembly 22, when in the inoperative position, between the cleaning means 24 and the sampling station 18. The moving means 26 includes a post 72 operatively mounted adjacent the tray 14 for limited up and down motion and for limited lateral motion, but only when it is also in the up position. An arm 74 is adjustably secured at one end about the post 72. The other end of the arm 74 is detachably secured about the member 20 carrying the tube assembly 22. Preferably, a further and shorter arm 76 also is attached to the arm 74 and normal thereto. This arm 76 is designed to carry a mixer blade 78, shown in phantom lines in FIG. 5, secured to the arm 76 in parallel spaced relation to the tube assembly 22 and being about coextensive in length therewith. The function of this mixer blade 78 is twofold: first, when at the sampling station 18, it is designed to enter and agitate a sample 80 in a sample container 16a next in line for sampling, note the arrow 82 indicating the direction of motion of the sample containers 16; second, when in the cleaning means 24, it is intended to stir the cleaning solution so as to facilitate and speed up the removal of the remnants of the just measured sample from about the tip 84 of the tube assembly 22.

Figure 5:
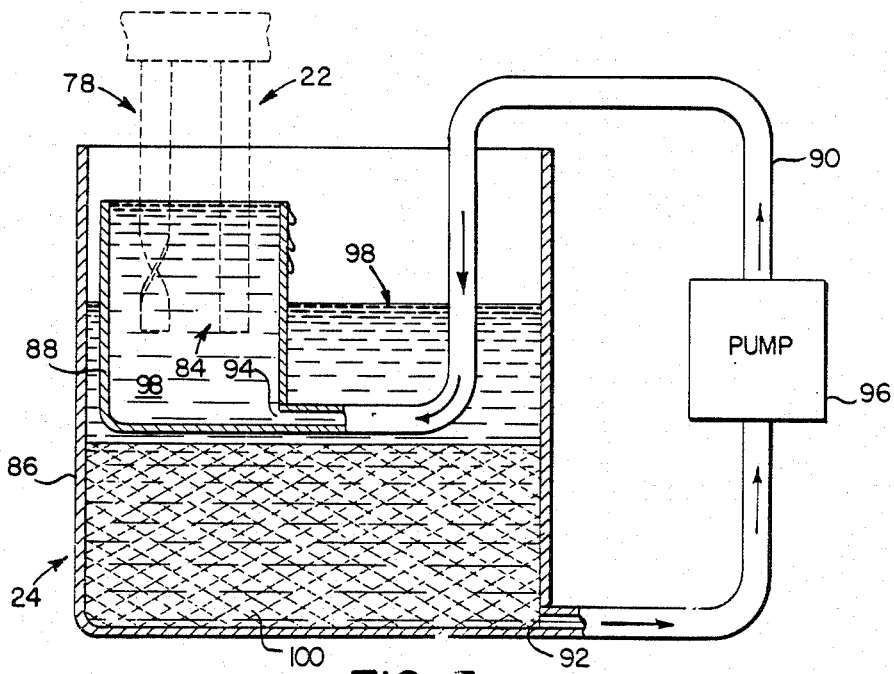
FIG. 5 is a vertical schematic, illustrating still further portions of the automatic sampling system shown in FIG. 1.

The cleaning means 24 preferably comprises a large container 86 and a small container 88 disposed within the large container 86, substantially as shown in FIG. 5. A flexible tubing 90 is connected between respective bottom openings 92 and 94 formed in the containers 86 and 88, establishing fluid communication between the containers 86 and 88. A suitable electric pump 96 is connected to the tubing 90. An appropriate cleaning solvent 98 is continuously being circulated by the pump 96 between the containers 86 and 88, more specifically from the bottom of the large container 86 into the bottom of the small container 88. Consequently, the small container 88 always is filled to the brim and in fact constantly overflows into the large container 86, which preferably is about three-quarters full. The bottom half or thereabout of the large container 86 preferably is filled with a suitable filter material 100 designed to trap the remnants of samples being washed off the tip 84 of the tube assembly 22. Most of these remnants go over the brim of the small container 88 during the overflow and hence gradually sink to the bottom of the large container 86. The sample remnants thus are carried into the filter material 100, together with the continuously circulating solvent 98, and are trapped therein. Of course, after certain amount of use, the filter material 100 will have to be changed, together with the cleaning solvent 98 to retain the reliability and sensitivity of measurements of the instrument 12.

In operation, the automatic sampling system 10 for introducing diluted viscous samples into the instrument 12 works as follows. The preferred sample tray 14 has a capacity for carrying up to one hundred fourteen sample containers 16. The containers 16 preferably are arranged in nineteen racks of six containers 16 each. Non-diluted viscous samples 80 are introduced into the sample containers 16 prior to the racks being placed onto the tray 14. Such non-diluted (i.e., not chemically pretreated) viscous samples 80 include oils, such as used engine oil from the crankcase of a truck or automobile, brines, sludges, plating solutions and the like, taken as is and introduced into the respective and appriorately marked containers 16. Due to the viscous nature of the samples 80, the containers 16 preferably are of the maximum diameter size, that is 18 mm. However, since the samples 80 are non-diluted, i.e., no organic solvents are added thereto while in the containers 16, the containers 16 may be made from a wider range of materials than otherwise would be the case. For example, the containers 16 can be made as disposables from inexpensive polymeric materials. Such polymeric materials however could not be used if the samples 80 were to be diluted with a diluent in the containers 16 themselves.

With the tray 14 loaded with containers 16 carrying viscous samples 80 to be analyzed for trace elements by the instrument 12, the instrument 12 is activated in the normal known manner, with its internal computer or microprocessor taking over its operations, aided as need be by manual entry at the keyboard. The tray 14 now automatically presents the first sample container 16 to the sampling station 18. During all this time, the tip 84 of the tube assembly 22 is in its normal rest position, namely within the cleaning solvent 98 contained within the small container 88 of the cleaning means 24. With the peristaltic pumps 68 and 70 constantly working, and working at different rates, cleaning solvent 98 will be aspirated into the tube assembly 22 at one rate, the lower rate, and a diluent 102, contained in a large diluent bottle 104, will also be aspirated into the tube assembly 22 via the flexible tubing 66 and at the higher rate. The location of the diluent bottle 104 is not critical. For the most part, it will be located at the bottom of the instrument 12 behind a convenient door for easy access and replacement, when empty or low on diluent 102. As mentioned, the dilution ratio is selectively adjustable by simply changing the pump tubings of the pumps 68 and/or 70. Preferably the ratio is two parts of diluent 102 to one part of solvent 98 or nine parts of diluent 102 to one part of solvent 98, or any preferred ratio therebetween. While diluent 102 and solvent 98 can, and frequently are, the same material, such as kerosene, xylene, hexane, methyl iso-butyl ketone, or dilute mineral acid or water as the case may be depending on the specific viscous sample 80, they need not be. Also, the relative strengths of the diluent 102 and solvent 98 may differ, depending upon the particular viscous samples 80 to be measured and/or the particular trace elements to be analyzed for by the instrument 12.

Figure 4:
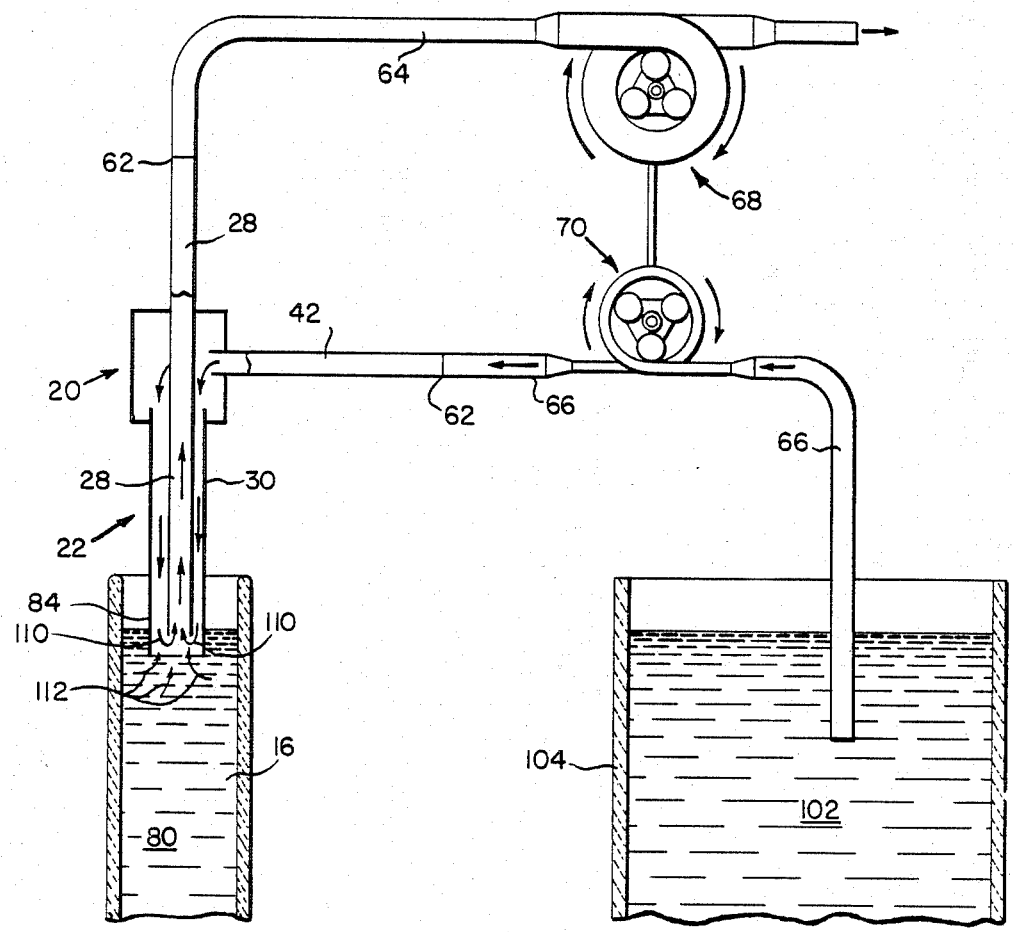
FIG. 4 is a vertical schematic, illustrating certain principles of operation of the automatic sampling system of the invention.

The above mentioned aspiration ratio of 3:1 or 10:1 or anything in between will hold true, of course, regardless of what fluid medium the tip 84 of the tube assembly 22 happens to be in. For, in addition to the tip 84 being in the solvent 98, it can also be in the air as when it is moved from the cleaning means 24 to the sampling station 18, and of course the tip 84 is in the viscous sample 80, when sampling. During the time that the tip is in motion from the cleaning means 24 to the sampling station 18, the tube assembly 22 will aspirate two (or nine or in between) parts of diluent 102 to one part of air. Due to the higher pumping rate of the pump 68 than that of the pump 70, all of the diluent 102 will be completely drawn into and up through the tube assembly 22, preventing thereby any diluent 102 from dripping onto either the tray 14 or any other part of the instrument 12. And during sampling, as illustrated in FIG. 4, the tube assembly 22 aspirates two (or nine or in between) parts of diluent 102 to one part of viscous sample 80, such as for example, spent engine oil.

Once the instrument 12, more particularly its computer, gives the command for sampling, the moving means 26 is actuated. This in turn will raise the post 72 and thereby the arm 74, the member 20 and the tube assembly 22 upward into its inoperative position in which its tip 84 is above and thus clear of the brim of the larger container 86. With the tube assembly 22 in its inoperative position, the moving means 26 will swing the tube assembly 22 and its associated mixer blade 78 in an arc of about 90° over the in line sample container 16 that happens to be at the sampling station 18, observe FIG. 2. Then, the tube assembly 22 is moved by the post 72 from its inoperative "up" position to its operative "down" position. In this operation position, the tip 84 of the tube assembly will have entered the viscous sample 80 in the container 16, substantially as shown in FIG. 4. At the same time, the mixer blade 78 carried by the further arm 76 will have entered the next in line container 16a to agitate the viscous sample 80 contained therein. Although it has been observed that suspended solids for the most part do not settle out, as would clearly be the case if the samples 80 in the containers 16 were diluted, some advance agitation can make sure that they do not.

Sampling now is effected. The dwell time for sampling is adjustable. Preferably, sample aspiration and analysis take between about 18 to about 20 seconds. During all this time, the tip 84 of the tube assembly 22 remains in the sample 80 and continues to aspirate the same in the same ratio mentioned above. With sampling and analysis done, the results appear at the display 106 of the instrument 12. The results preferably also are printed on a running tape 108 for later use. At this point, the tip 84 of the tube assembly 22 is withdrawn from the just-analyzed viscous sample 80 and is returned into the cleaning solvent 98 of the cleaning means 24. Of course, the mixer blade 78 also is moved along with the tube assembly 22 and into the cleaning solvent 98 adjacent the tube assembly 22, where it will now contribute effectively to clean the outside of the tip 84 thereof. The preferred dwell time for cleaning, when running a multiplicity of samples 80, is about 18 seconds, which also is adjustable. This results in a sample throughput of about 100 samples per hour.

Sample dilution and mixing in the above-mentioned ratio of 3:1 to 5:1 is facilitated, in addition to the different sizes of pump tubings for the pumps 68 and 70, by the above-mentioned offset by the distance 38 separating the free end 36 of the inner tube 28 from the free end 40 of the outer tube 30, note FIG. 3 again. Preferably, the offset distance 38 is no less than three millimeters and can range to about fifteen to twenty millimeters. The longer this offset distance 38, the more tube area, both inside and outside the tubes, that needs to be cleaned in between sampling. As mentioned, the position of the inner tube 28, hence the extent of this distance 38 and thus the depth of penetration by the tube's end 36 into the sample 80, is adjustable within the member 20 by loosening the top metal part 46. Such adjustment may be desirable when changing over to analyze a different viscous sample 80, for example changing from engine oil to brine or sludge. For, the depth of penetration of the viscous sample 80 by the free end 36 of the inner tube 28 affects the degree of diluent 102 to sample 80 interaction. As may be observed in FIGS. 3 and 4, sample dilution, for the most part, takes place in the tip 84 of the tube assembly 22, observe the arrows 110 indicating the incoming diluent 102 and the arrows 112 the aspirating viscous sample 80. Mixing of the diluted sample, both in the tip 84 and as it proceeds along the length of the tube assembly 22, also is aided: by turbulent flow, generated by the relative high speed of the diluent 102 as it is propelled through the small pump tubing of the pump 70 and into the tip 84, by the expansion of the diluted sample from the flexible tubing 64 into the wider pump tubing of the pump 68, and by the compression of the diluted sample from the wider pump tubing of the pump 68 back into the smaller flexible tubing 64 leading to the nebulizer of the instrument 12. The final mixing of the diluted sample, of course, takes place in the nebulization chamber itself.

It will be appreciated that in between the several diluted samples being aspirated up and through the tube assembly 22 during a run, there will be segments (slugs) comprising first a mixture of diluent 102 and air, then diluent 102 and cleaning solvent 98, and then again diluent 102 and air, with air being aspirated during the movement of the tube assembly 22 between the sampling station 18 to the cleaning means 24 and back again. These segments or slugs separating adjacent diluted viscous samples effectively eliminate any crossover in analysis between successive samples.

Thus it has been shown and described an automatic sampling system 10 and method for introducing, seriatim, a plurality of diluted viscous samples into an instrument 12 for analysis for trace elements, which system 10 and method satisfy the objects and advantages set forth above.

Since certain changes may be made in the present disclosure without departing from the scope of the present invention, it is intended that all matter described in the foregoing specification or shown in the accompanying drawings, be interpreted in an illustrative and not a limiting sense.

What is claimed is:

1. A sampling system comprising:

(a) a tube assembly mounted in a member, said member formed of two parts: a resilient part having an upper dome-shaped end, a lower end and provided with a stepped, internal bore extending concentrically therethrough, said resilient part also having an externally-threaded upper portion near said dome-shaped portion, and a rigid part having an internally-threaded cylindrical portion and a central beveled portion designed to fit over and to mesh with said externally-threaded portion and said dome-shaped portion of said resilient part;

(b) said tube assembly including an inner tube extending through and beyond said ends of said resilient part and terminating in a first end and a second end, and an outer tube concentrically spaced about said inner tube and having first and second ends, said tubes being received within said stepped bore of said resilient part, said first ends of said inner and said outer tubes being offset from one another, and said second end of said outer tube terminating in said stepped bore;

(c) said rigid part designed to compress said resilient part, particularly its said dome-shaped portion about said inner tube so as to adjust and to fix the extent of said offset of said inner tube and said outer tube first ends; and (d) a further tube mounted in said member at an angle to and communicating with the space defined between said inner and said outer tube and having a free end.

2. The sampling system of claim 1 wherein said inner tube, said concentric outer tube and said further tube are all made of a rigid material.

3. The sampling system of claim 1 further including a pair of flexible tubing, one of said flexible pair of tubing connected to said second end of said inner tube and the other of said flexible pair of tubing connected to said free end of said further tube, and a pair of peristalic pumps pumping at different rates, one of said pair of peristalic pumps with a slower rate connected to said one of said pair of flexible tubing which is connected to said further tube, and the other of said pair of peristaltic pumps with a higher rate connected to said other of said pair of flexible tubing which is connected to said inner tube, and means for moving said tube assembly in translation between an operative position and an inoperative position and also for moving said tube assembly when in said inoperative position between two stations, and a mixer blade operatively mounted in spaced apart parallel relation to and adjacent said tube assembly and designed for concurrent movement therewith.

4. An automatic sampling system for introducing a diluted viscous sample, including organic and aqueous samples such as oils, brines, sludges, plating solutions, into an instrument for analysis of trace elements, including wear metals and other elements such as calcium, barium, zinc, sodium, magnesium, boron and phosphor, said sampling system comprising:

(a) a tray designed to hold a plurality of sample containers and to present said containers seriatim to a sampling station;

(b) a member operatively mounted adjacent said samping station, said member formed of two parts: a resilient male part having an upper, smooth dome-shaped portion, an externally-threaded cylindrical portion near said dome-shaped portion, and a stepped bore extending concentrically therethrough, and a rigid part having a central beveled portion designed to fit over and to mesh with said dome-shaped portion and an internally-threaded cylindrical portion designed to mesh with said externally-threaded cylindrical portion of said resilient male part;

(c) a tube assembly secured in said stepped bore of said member and including an inner tube having first and second ends and an outer tube having first and second ends, said outer tube being concentric about said inner tube, said inner tube extending through said member in two direction and said outer tube in but one direction, said first ends of said inner and said outer tubes being offset from one another and said second end of said outer tube terminating in said stepped bore;

(d) a further tube also secured in said member at an angle to and communicating with the space defined between said inner and said outer tube and having a free end;

(e) cleaning means mounted adjacent said sampling station for cleaning said first ends of said inner and outer tubes;

(f) means for moving said tube assembly between an operative position and an inoperative position and also for moving said tube assembly when in said inoperative position between said sampling station and said cleaning means;

(g) a mixer blade operatively mounted in spaced apart relation to and adjacent said tube assembly and designed for concurrent movement therewith between said sampling station and said cleaning means;

(h) said rigid part of said member designed to compress said dome-shaped portion of said resilient part about said inner tube so as to adjust and to fix the extent of said offset between the first ends of said inner and said outer tubes.

5. The automatic sampling system of claim 4 wherein said cleaning means includes a large container having a bottom and an opening level with said bottom and a small container disposed within said large container also having a bottom and an opening level with said bottom, a flexible tubing establishing fluid communication between said openings, and pump means connected to said tubing for continuously circulating a fluid between said containers.

6. The automatic sampling system of claim 4 wherein said first ends of said inner and outer tubes in said operative position are designed to enter a viscous sample contained in one of said plurality of sample containers and said mixer blade is designed to enter a viscous sample contained in an adjacent one of said plurality of sample containers when at said sampling station and both said free ends of said tubes and said mixer blade are designed to enter said cleaning means when moved to said cleaning means.

* * * * *